United States Patent
Steven et al.

(10) Patent No.: US 9,427,156 B1
(45) Date of Patent: Aug. 30, 2016

(54) DEVICES AND METHODS FOR WAVEFRONT SENSING AND CORNEAL TOPOGRAPHY

(71) Applicant: Ovitz Corporation, West Henrietta, NY (US)

(72) Inventors: Samuel J. Steven, Rochester, NY (US); Joung Yoon Kim, Seoul (KR)

(73) Assignee: OVITZ CORPORATION, West Henrietta, NY (US)

( * ) Notice: Subject to any disclaimer, the term of this patent is extended or adjusted under 35 U.S.C. 154(b) by 0 days.

(21) Appl. No.: 14/928,063

(22) Filed: Oct. 30, 2015

Related U.S. Application Data

(60) Provisional application No. 62/210,893, filed on Aug. 27, 2015.

(51) Int. Cl.
| | | |
|---|---|---|
| *A61B 3/14* | (2006.01) | |
| *A61B 3/18* | (2006.01) | |
| *A61B 3/107* | (2006.01) | |
| *A61B 3/10* | (2006.01) | |
| *A61B 3/00* | (2006.01) | |
| *G02B 5/02* | (2006.01) | |
| *G02B 27/10* | (2006.01) | |
| *G02B 3/00* | (2006.01) | |

(52) U.S. Cl.
CPC ............ *A61B 3/18* (2013.01); *A61B 3/0025* (2013.01); *A61B 3/0083* (2013.01); *A61B 3/107* (2013.01); *A61B 3/1015* (2013.01); *A61B 3/14* (2013.01); *G02B 5/0263* (2013.01); *A61B 2560/0431* (2013.01); *G02B 3/0006* (2013.01); *G02B 27/10* (2013.01)

(58) Field of Classification Search
CPC ...... A61B 3/103; A61B 3/1015; A61B 3/14; A61B 3/12; A61B 3/125; A61B 3/117
USPC ................ 351/205, 206, 219, 246
See application file for complete search history.

(56) References Cited

U.S. PATENT DOCUMENTS

| | | | | |
|---|---|---|---|---|
| 6,142,630 | A * | 11/2000 | Koester | .......... 351/219 |
| 2003/0142271 | A1 | 7/2003 | Ross et al. | |
| 2004/0189942 | A1 | 9/2004 | Yoon | |
| 2014/0347629 | A1* | 11/2014 | Donitzky et al. | .......... 351/206 |

OTHER PUBLICATIONS

Zhou, Fan, "Combined Corneal Topographer and Aberrometer Based on Shack-Hartmann Wavefront Sensing and its Clinical Applications on Human Eyes," submitted to the faculty of the University Graduate School in partial fulfillment of the requirements for the degree Doctor of Philosophy in the School of Optometry, Indiana University, Aug. 2004, 247 pgs.

* cited by examiner

*Primary Examiner* — James Greece
(74) *Attorney, Agent, or Firm* — Morgan, Lewis & Bockius LLP

(57) ABSTRACT

Devices and methods for wavefront sensing and keratometry are described. A device includes a lens assembly, a wavefront sensor, and a keratometer. The wavefront sensor includes: the lens assembly; a first light source configured to emit first light and transfer the first light emitted from the first light source toward an eye through the lens assembly; an array of lenses that is distinct from the lens assembly; and a first image sensor configured to receive light, from the eye, transmitted through the lens assembly and the array of lenses. The keratomer includes: the lens assembly; a second light source that is distinct from the first light source and configured to emit second light and transfer the second light emitted from the second light source toward the eye; and a second image sensor configured to receive light, from the eye, transmitted through the lens assembly.

18 Claims, 11 Drawing Sheets

```
                                                              ┌─ 500
                                                             ✓
┌─────────────────────────────────────────────────────────────────────────┐
│ 502  Initiate a first light source to emit first light, wherein the light emitted from the │
│      first light source is transferred toward an eye through a lens assembly            │
└─────────────────────────────────────────────────────────────────────────┘
                                      ↓
┌─────────────────────────────────────────────────────────────────────────┐
│ 504  While the first light source emits the first light, receive, at a first image sensor, │
│   a first image of light from the eye, transferred through the lens assembly and an      │
│                                  array of lenses                                           │
└─────────────────────────────────────────────────────────────────────────┘
                                      ↓
┌─────────────────────────────────────────────────────────────────────────┐
│ 506  Initiate a second light source to emit second light, wherein the light emitted    │
│          from the second light source is transferred toward the eye                      │
└─────────────────────────────────────────────────────────────────────────┘
                                      ↓
┌─────────────────────────────────────────────────────────────────────────┐
│ 508  While the second light source emits the second light, receive, at a second        │
│ image sensor, a second image of light from the eye, transferred through the lens       │
│                                    assembly                                              │
│  ┌ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┐  │
│  │ 510  In conjunction with receiving the second image of the light from the eye, │  │
│  │           collect an image of the eye with the second image sensor              │  │
│  │  ┌ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┐    │  │
│  │  │  512  Confirm whether a location of the eye satisfies predefined  │    │  │
│  │  │                         alignment criteria                          │    │  │
│  │  └ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┘    │  │
│  │                                                                                  │  │
│  │  ┌ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┐    │  │
│  │  │  514  Determine a position of the eye from the image of the eye   │    │  │
│  │  │  collected with the second image sensor; and adjust one or more   │    │  │
│  │  │  aberrations associated with the eye based on the position of the eye │ │  │
│  │  │ determined from the image of the eye collected with the second image│    │  │
│  │  │                                sensor                                │    │  │
│  │  └ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┘    │  │
│  │                                                                                  │  │
│  │  ┌ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┐    │  │
│  │  │  516  Determine a size of a pupil of the eye from the image of the eye │    │  │
│  │  │                collected with the second image sensor                  │    │  │
│  │  └ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┘    │  │
│  └ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┘  │
└─────────────────────────────────────────────────────────────────────────┘

┌ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┐
│ 518  Analyze the first image and determining one or more aberrations associated   │
│   with the eye; and analyze the second image and determining a curvature of a     │
│                                  cornea of the eye                                   │
│                                                                                       │
│   ┌ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┐  │
│   │ 520  Analyzing the first image and determining the one or more aberrations │  │
│   │ associated with the eye include executing a predefined set of instructions for │  │
│   │    analyzing an image that includes an array of spots.  Analyzing the second   │  │
│   │    image and determining the curvature of the cornea of the eye also include   │  │
│   │       executing the predefined set of instructions for analyzing an image that  │  │
│   │                            includes an array of spots                            │  │
│   └ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┘  │
└ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ─ ┘
```

Figure 5

DEVICES AND METHODS FOR WAVEFRONT SENSING AND CORNEAL TOPOGRAPHY

RELATED APPLICATION

This application claims priority to, and benefit of, U.S. Provisional Patent Application Ser. No. 62/210,893, filed Aug. 27, 2015, entitled "Devices and Methods for Wavefront Sensing and Corneal Topography," which is incorporated by reference herein in its entirety.

TECHNICAL FIELD

This application relates generally to wavefront sensing and corneal topography, and more particularly, portable devices that are capable of performing both wavefront sensing and corneal topography.

BACKGROUND

Eyes are important organs, which play a critical role in human's visual perception. An eye has a roughly spherical shape and includes multiple elements, such as cornea, lens, vitreous humour, and retina. Imperfections in these components can cause reduction or loss of vision. For example, too much or too little optical power in the eye can lead to blurring of the vision (e.g., near-sightedness and far-sightedness), and astigmatism can also cause blurring of the vision. Because the cornea is responsible for a significant portion of the eye's optical power, it is also important to accurately measure its topography. In addition, corneal topography provides important information for laser refractive surgery.

Both wavefront sensors and corneal topographers are important tools in ophthalmology. Wavefront sensors provide information indicating one or more aberrations in the eye. In particular, wavefront sensors have an advantage over auto-refractors in that wavefront sensors can measure higher order aberrations. Various corneal topographers (e.g., Placido topographers) are used for measuring the shape of cornea. An early intervention of visual impairment through an early diagnosis may allow reversal, or control over further progression of, such visual impairment. It is believed that almost 80% of visual impairment cases are preventable with proper diagnosis and intervention.

However, diagnostic instruments that can perform both wavefront sensing and corneal topography are not readily available, partly due to their sizes and costs. Especially, many children do not receive the eye care they need, and they are at the greatest risk of undetected vision problem. A portable device that can perform both wavefront sensing and corneal topography is expected to allow wider and more frequent screening for visual impairments, which will prevent a great number of visual impairment cases.

SUMMARY

Accordingly, there is a need for portable devices that can perform both wavefront sensing and corneal topography. Such devices and related methods optionally complement or replace conventional devices and methods. Such devices provide portability, performance, and convenience that are not available from conventional devices and methods.

The above deficiencies and other problems associated with conventional devices and corresponding methods are reduced or eliminated by the disclosed devices.

As described in more detail below, some embodiments involve a portable device that includes a lens assembly, a wavefront sensor, and a keratomer. The wavefront sensor includes: the lens assembly; a first light source configured to emit first light and transfer the first light emitted from the first light source toward an eye through the lens assembly; an array of lenses that is distinct from the lens assembly; and a first image sensor configured to receive light, from the eye, transmitted through the lens assembly and the array of lenses. The keratomer includes: the lens assembly; a second light source that is distinct from the first light source and configured to emit second light and transfer the second light emitted from the second light source toward the eye; and a second image sensor configured to receive light, from the eye, transmitted through the lens assembly.

In some embodiments, the second light source is configured to transfer the second light emitted from the second light source toward the eye without transmitting the second light emitted from the second light source through the lens assembly.

In some embodiments, the second light source is configured to project an array of spots on the eye.

In some embodiments, the second light source includes a diffuser with a spot array pattern and one or more light emitters placed behind the diffuser and configured to emit light toward the diffuser.

In some embodiments, the second light source includes a diffuser with a spot array pattern and one or more light emitters and one or more reflectors arranged to send light toward the diffuser from behind the diffuser.

In some embodiments, the second light source includes a diffuser with a spot array pattern and a plurality of light emitters placed along a periphery of the diffuser. At least a first portion of the diffuser is transparent and at least a second portion of the diffuser is configured to diffuse light.

In some embodiments, the lens assembly includes a lens that is tilted from an optical axis of the device.

In some embodiments, the first light source is configured to transfer the first light emitted from the first light source off an optical axis of the device.

In some embodiments, the first image sensor is configured to receive the light from the eye while the first light source emits the first light.

In some embodiments, the second image sensor is configured to receive the light from the eye while the second light source emits the second light.

In some embodiments, the lens assembly is a doublet lens.

In some embodiments, the lens assembly includes two or more separate lenses.

In some embodiments, the device includes a beam steerer configured to transfer light from the eye, transmitted through the lens assembly, toward the first image sensor and/or the second image sensor.

In some embodiments, the beam steerer is a beam splitter.

In some embodiments, the device includes an eyecup configured to position the eye relative to the device.

In accordance with some embodiments, a portable device includes a wavefront sensor and a keratometer. The wavefront sensor includes a first light source configured to emit first light and transfer the first light emitted from the first light source toward an eye through the lens assembly; an array of lenses; and a first image sensor configured to receive light, from the eye, transmitted through the lens assembly and the array of lenses. The keratomer includes a second light source that is distinct from the first light source and configured to emit second light and transfer the second light emitted from the second light source toward the eye. The second light source is configured to project an array of spots on the eye. The keratometer also includes a second image sensor configured to receive light, from the eye, transmitted through the lens assembly.

In accordance with some embodiments, a method includes transferring first light emitted from a first light source toward the eye through a lens assembly; and, in response to transferring the first light emitted from the first light source toward the eye through a lens assembly: transferring light from the eye through the lens assembly and an array of lenses; and receiving the light from the eye, transferred through the lens assembly and the array of lenses, at a first image sensor. The method also includes transferring second light emitted from a second light source toward the eye; and, in response to transferring the second light emitted from the second light source toward the eye: transferring light from the eye through the lens assembly; and receiving the light from the eye, transferred through the lens assembly, at a second image sensor. The method further includes analyzing the light received at the first image sensor and determining one or more aberrations associated with the eye; providing information that indicates the one or more aberrations associated with the eye; analyzing the light received at the second image sensor and determining a curvature of a cornea of the eye; and providing information that indicates the curvature of the cornea of the eye.

In accordance with some embodiments, an electronic device includes one or more processors; and memory storing one or more programs. The one or more programs include instructions for initiating a first light source to emit first light. The first light emitted from the first light source is transferred toward an eye through a lens assembly. The one or more programs also include instructions for, while the first light source emits the first light, receiving, at a first image sensor, a first image of light from the eye, transferred through the lens assembly and an array of lenses; initiating a second light source to emit second light. The second light emitted from the second light source is transferred toward the eye. The one or more programs further include instructions for, while the second light source emits the second light, receiving, at a second image sensor, a second image of light from the eye, transferred through the lens assembly.

In accordance with some embodiments, a method is performed at an electronic device that includes one or more processors and memory storing instructions for execution by the one or more processors. The method includes initiating a first light source to emit first light. The first light emitted from the first light source is transferred toward an eye through a lens assembly. The method also includes, while the first light source emits the first light, receiving, at a first image sensor, a first image of light from the eye, transferred through the lens assembly and an array of lenses; initiating a second light source to emit second light. The second light emitted from the second light source is transferred toward the eye. The method further includes, while the second light source emits the second light, receiving, at a second image sensor, a second image of light from the eye, transferred through the lens assembly.

In accordance with some embodiments, a computer readable storage medium stores one or more programs for execution by one or more processors of an electronic device. The one or more programs include instructions, which, when executed by the one or more processors of the electronic device, cause the device to initiate a first light source to emit first light. The first light emitted from the first light source is transferred toward an eye through a lens assembly. The one or more programs also include instructions, which, when executed by the one or more processors of the electronic device, cause the device to, while the first light source emits the first light, receive, at a first image sensor, a first image of light from the eye, transferred through the lens assembly and an array of lenses; initiate a second light source to emit second light. The second light emitted from the second light source is transferred toward the eye. The one or more programs further include instructions, which, when executed by the one or more processors of the electronic device, cause the device to, while the second light source emits the second light, receive, at a second image sensor, a second image of light from the eye, transferred through the lens assembly.

Thus, portable devices that include both wavefront sensors and corneal topographers are provided with faster, more efficient methods for performing wavefront sensing and corneal topography, thereby increasing the effectiveness, efficiency, portability, and user satisfaction with such devices. Such devices and corresponding methods may complement or replace conventional methods for performing wavefront sensing and corneal topography.

BRIEF DESCRIPTION OF THE DRAWINGS

For a better understanding of the various described embodiments, reference should be made to the Description of Embodiments below, in conjunction with the following drawings in which like reference numerals refer to corresponding parts throughout the figures.

FIG. 5 is a flowchart representing a method of optical measurements with a portable device, in accordance with some embodiments.

DESCRIPTION OF EMBODIMENTS

Figure 1A:
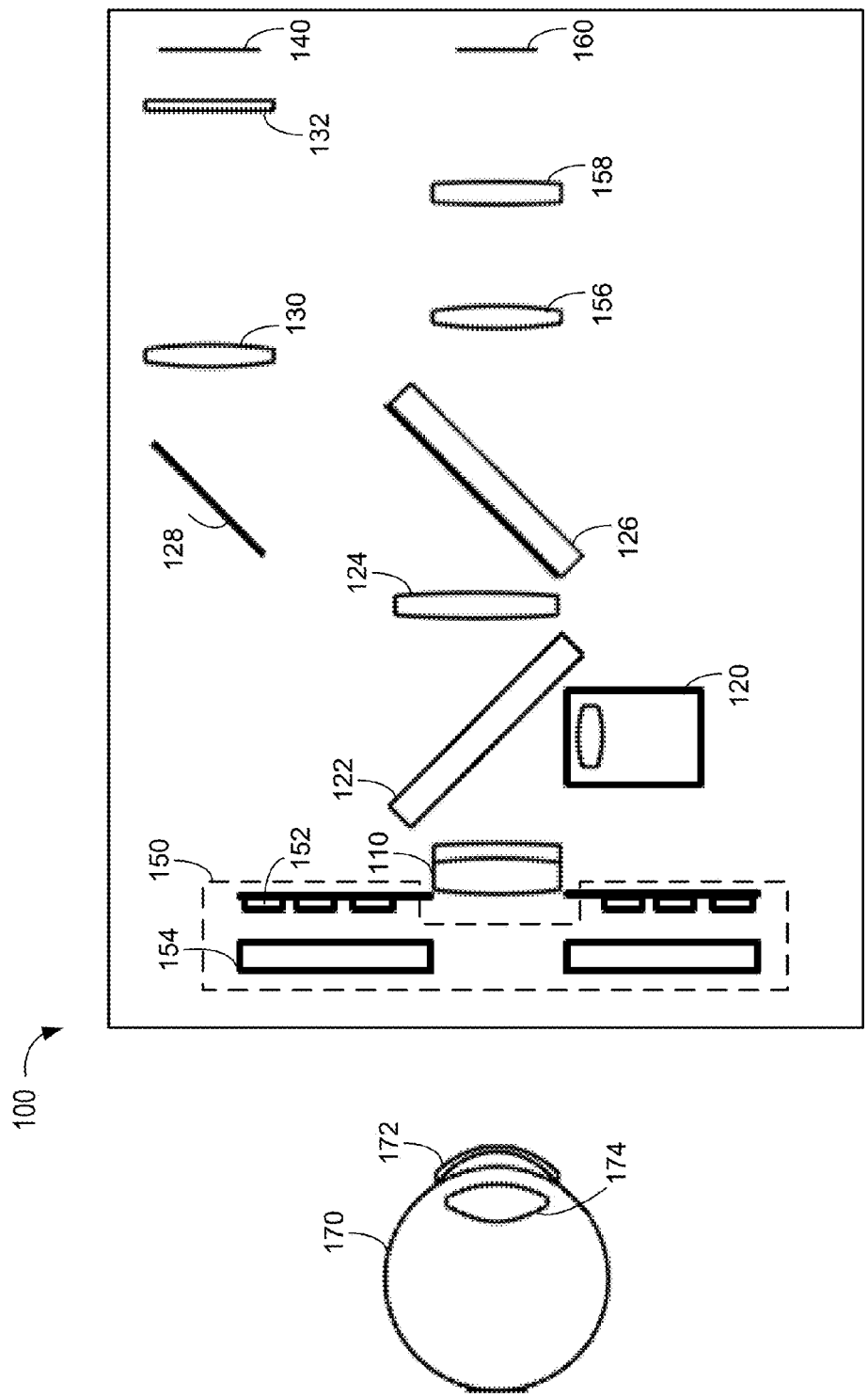
FIG. 1A illustrates optical components of a portable device in accordance with some embodiments.

Conventional wavefront sensors are widely used for detecting one or more aberrations of an eye. Conventional corneal topographers are used for determining a profile of a cornea. However, conventional devices that can perform both wavefront sensing and corneal topography have not been made portable. It is not simply the size of the conventional devices that has prevented miniaturization of such devices. Rather, the inventors of this application have observed that the conventional devices, if just reduced in size, would suffer from significant errors. The inventors of this application have discovered that the errors are mainly due to the positioning of the eye relative to the pupil plane of a device. Conventional devices include a bulky mechanism for aligning the position of an eye so that the eye is positioned on the pupil plane. However, such a bulky mechanism cannot be used in portable devices, and without the alignment mechanism, significant errors were observed in miniaturized devices. The inventors of this application have discovered that a new optical design, which includes a lens assembly in a particular position, significantly reduces the impact of the positioning error. Portable devices with such lens assemblies can perform both wavefront sensing and corneal topography with superior performance compared to conventional devices.

Reference will be made to embodiments, examples of which are illustrated in the accompanying drawings. In the following description, numerous specific details are set forth in order to provide a thorough understanding of the various described embodiments. However, it will be apparent to one of ordinary skill in the art that the various described embodiments may be practiced without these particular details. In other instances, methods, procedures, components, circuits, and networks that are well-known to those of ordinary skill in the art are not described in detail so as not to unnecessarily obscure aspects of the embodiments.

It will also be understood that, although the terms first, second, etc. may be used herein to describe various elements, these elements should not be limited by these terms. These terms are only used to distinguish one element from another. For example, a first image sensor could be termed a second image sensor, and, similarly, a second image sensor could be termed a first image sensor, without departing from the scope of the various described embodiments. The first image sensor and the second image sensor are both image sensors, but they are not the same image sensor.

The terminology used in the description of the embodiments herein is for the purpose of describing particular embodiments only and is not intended to be limiting of the invention. As used in the description of the invention and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting (the stated condition or event)" or "in response to detecting (the stated condition or event)," depending on the context.

FIG. 1A illustrates optical components of portable device 100 in accordance with some embodiments.

Device 100 includes lens assembly 110. In some embodiments, lens assembly 110 is a doublet lens, as shown in FIG. 1A. For example, a doublet lens is selected to reduce spherical aberration and other aberrations (e.g., coma and/or chromatic aberration). In some embodiments, lens assembly 110 is a triplet lens. In some embodiments, lens assembly 110 is a singlet lens. In some embodiments, lens assembly 110 includes two or more separate lenses. In some embodiments, lens assembly 110 includes an aspheric lens. In some embodiments, a working distance of lens assembly 110 is between 10-100 mm (e.g., between 10-90 mm, 10-80 mm, 10-70 mm, 10-60 mm, 10-50 mm, 15-90 mm, 15-80 mm, 15-70 mm, 15-60 mm, 15-50 mm, 20-90 mm, 20-80 mm, 20-70 mm, 20-60 mm, 20-50 mm, 25-90 mm, 25-80 mm, 25-70 mm, 25-60 mm, or 25-50 mm). In some embodiments, an effective focal length of a first lens (e.g., the lens positioned closest to the pupil plane) is between 10-150 mm (e.g., between 10-140 mm, 10-130 mm, 10-120 mm, 10-110 mm, 10-100 mm, 10-90 mm, 10-80 mm, 10-70 mm, 10-60 mm, 10-50 mm, 15-150 mm, 15-130 mm, 15-120 mm, 15-110 mm, 15-100 mm, 15-90 mm, 15-80 mm, 15-70 mm, 15-60 mm, 15-50 mm, 20-150 mm, 20-130 mm, 20-120 mm, 20-110 mm, 20-100 mm, 20-90 mm, 20-80 mm, 20-70 mm, 20-60 mm, 20-50 mm, 25-150 mm, 25-130 mm, 25-120 mm, 25-110 mm, 25-100 mm, 25-90 mm, 25-80 mm, 25-70 mm, 25-60 mm, 25-50 mm, 30-150 mm, 30-130 mm, 30-120 mm, 30-110 mm, 30-100 mm, 30-90 mm, 30-80 mm, 30-70 mm, 30-60 mm, 30-50 mm, 35-150 mm, 35-130 mm, 35-120 mm, 35-110 mm, 35-100 mm, 35-90 mm, 35-80 mm, 35-70 mm, 35-60 mm, 35-50 mm, 40-150 mm, 40-130 mm, 40-120 mm, 40-110 mm, 40-100 mm, 40-90 mm, 40-80 mm, 40-70 mm, 40-60 mm, 40-50 mm, 45-150 mm, 45-130 mm, 45-120 mm, 45-110 mm, 45-100 mm, 45-90 mm, 45-80 mm, 45-70 mm, 45-60 mm, 45-50 mm, 50-150 mm, 50-130 mm, 50-120 mm, 50-110 mm, 50-100 mm, 50-90 mm, 50-80 mm, 50-70 mm, or 50-60 mm). In some embodiments, for an 8 mm pupil diameter, the lens diameter is 16-24 mm. In some embodiments, for a 7 mm pupil diameter, the lens diameter is 12-20 mm. In some embodiments, the f-number of lens assembly is between 2 and 5. The use of a common lens assembly (e.g., lens assembly 110) in both a wavefront sensor and a corneal topographer allows the integration of the wavefront sensor and the corneal topographer without needing large diameter optics.

Device 100 also includes a wavefront sensor. In some embodiments, the wavefront sensor includes lens assembly 110, first light source 120, an array of lenses 132 (also called herein lenslets), and first image sensor 140. In some embodiments, the wavefront sensor includes additional components.

Figure 1B:
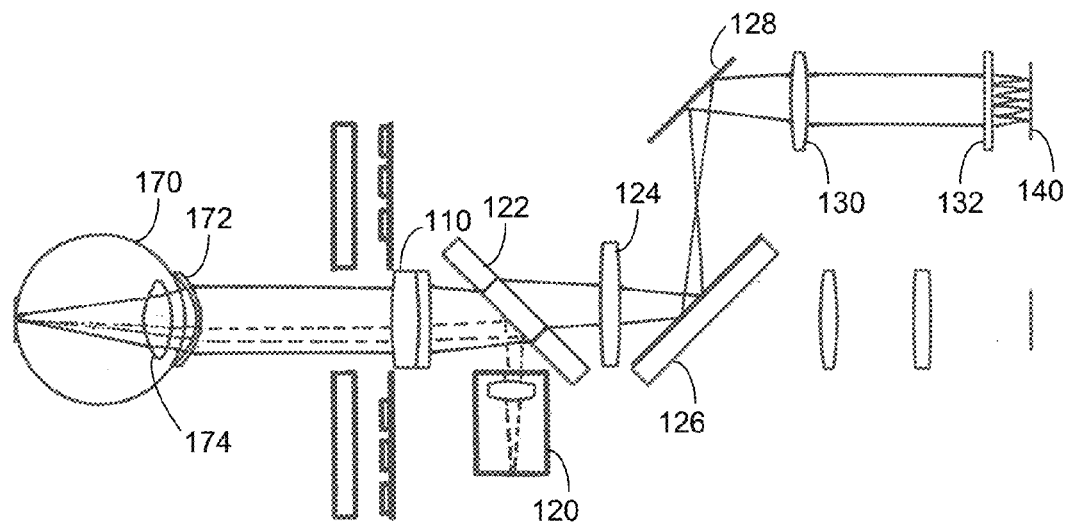
FIG. 1B illustrates wavefront sensing with the portable device shown in FIG. 1A, in accordance with some embodiments.

First light source 120 is configured to emit first light and transfer the first light emitted from the first light source toward eye 170 through lens assembly 110, as depicted in FIG. 1B.

Figure 1C:
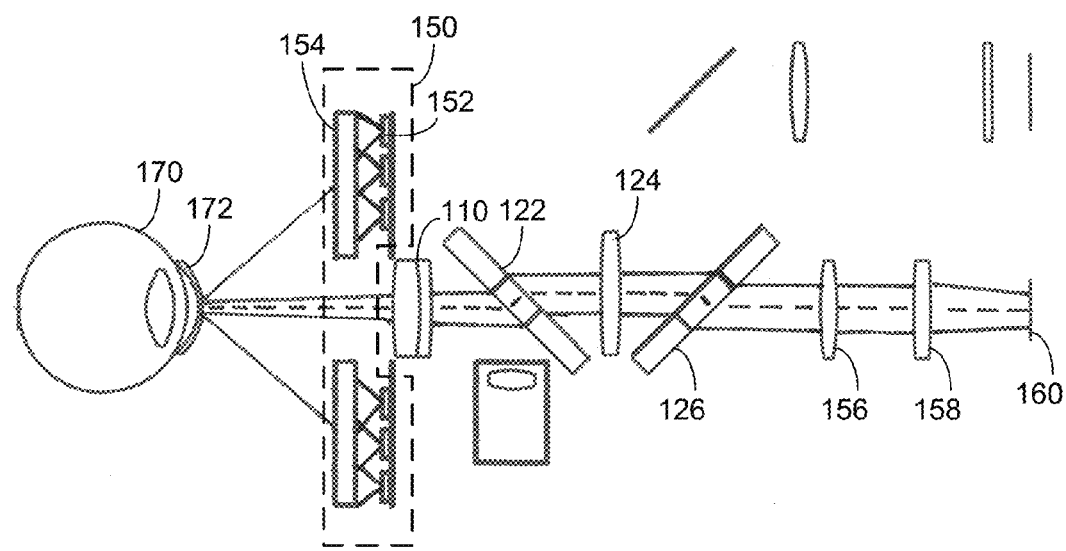
FIG. 1C illustrates corneal topography with the portable device shown in FIG. 1A, in accordance with some embodiments.

Although FIGS. 1A-1C include eye 170 and its components (e.g., cornea 172 and lens 174) to illustrate the operations of device 100 with eye 170, eye 170 and its components are not part of device 100.

Turning back to FIG. 1A, in some embodiments, first light source 120 is configured to emit light of a single wavelength or a narrow band of wavelengths. Exemplary first light source 120 includes a laser (e.g., a laser diode) or a light-emitting diode (LED).

In some embodiments, first light source 120 includes a lens (as shown in FIG. 1A) to change the divergence of the light emitted from first light source 120 so that the light, after passing through lens assembly 110, is collimated.

In some embodiments, first light source 120 includes a pinhole (e.g., having a diameter of 1 mm or less, such as 400 μm, 500 μm, 600 μm, 700 μm, 800 μm, 900 μm, and 1 mm).

Because lens assembly 110 is positioned closer to eye 170 than first light source 120 (e.g., light from first light source 120 passes through lens assembly 110), in some cases, it is important to reduce back reflection of the light at lens assembly. Thus, in some embodiments, an anti-reflection coating is applied on a back surface (and optionally, a front surface) of lens assembly 110 to reduce back reflection. In some embodiments, first light source 120 is configured to transfer the first light emitted from first light source 120 off an optical axis of device 100 (e.g., an optical axis of lens assembly 110), as shown in FIG. 1B (e.g., the first light emitted from first light source 120 propagates parallel to, and offset from, the optical axis of lens assembly 110). This reduces back reflection of the first light emitted from first light source 120, by lens assembly 110, toward first image sensor 140. In some embodiments, the wavefront sensor includes a quarter-wave plate to reduce back reflection, of the first light, from lens assembly 110 (e.g., light reflected from lens assembly 110 is attenuated by the quarter-wave plate). In some embodiments, lens assembly 110 includes a lens that is tilted from an optical axis of the device, to reduce back reflection, of the first light, from the tilted lens (e.g., by reflecting the light toward a direction that does not face first image sensor 140). In some embodiments, a curvature of a lens in lens assembly 110 is selected so that reflection, of the first light, from the lens is directed toward a direction that does not face first image sensor 140.

First image sensor 140 is configured to receive light, from eye 170, transmitted through lens assembly 110 and the array of lenses 132. In some embodiments, the light from eye 170 includes light scattered at a retina or fovea of eye 170 (in response to the first light from first light source 120). For example, as shown in FIG. 1B, light from eye 170 passes multiple optical elements, such as lens assembly 110, beam steerer 122, lens 124, beam steerer 126, mirror 128, and lens 130, and reaches first image sensor 140.

Beam steerer 122 is configured to reflect light from light source 120 and transmit light from eye 170, as shown in FIG. 1B. Alternatively, beam steerer 122 is configured to transmit light from light source 120 and reflect light from eye 170. In some embodiments, beam steerer 122 is a beam splitter (e.g., 50:50 beam splitter, polarizing beam splitter, etc.). In some embodiments, beam steerer 122 is a wedge prism, and when first light source 120 is configured to have a linear polarization, the polarization of the light emitted from first light source 120 is configured to reflect at least partly by the wedge prism. Light of a polarization that is perpendicular to the linear polarization of the light emitted from first light source 120 is transmitted through the wedge prism. In some cases, the wedge prism also reduces light reflected from cornea 172 of eye 170.

In some embodiments, beam steerer 122 is tilted at such an angle (e.g., an angle between the optical axis of device 100 and a surface normal of beam steerer 122 is at an angle less than 45°, such as 30°) so that the space occupied by beam steerer 122 is reduced.

In some embodiments, device 100 includes lenses 124 and 130 to modify a working distance of device 100.

The array of lenses 132 is arranged to focus incoming light onto multiple spots, which are imaged by first image sensor 140. As in Shack-Hartmann wavefront sensor, an aberration in a wavefront causes displacements (or disappearances) of the spots on first image sensor 140. In some embodiments, a Hartmann array is used instead of the array of lenses 132. A Hartmann array is a plate with an array of apertures (e.g., through-holes) defined therein.

In some embodiments, lens 124, lens 130, and the array of lenses 132 are arranged such that the wavefront sensor is configured to measure a reduced range of optical power. A wavefront sensor that is capable of measuring a wide range of optical power may have less accuracy than a wavefront sensor that is capable of measuring a narrow range of optical power. Thus, when a high accuracy in wavefront sensor measurements is desired, the wavefront sensor can be designed to cover a narrow range of optical power. For example, a wavefront sensor for diagnosing low and medium myopia can be configured with a narrow range of optical power between 0 and −6.0 diopters, with its range centering around −3.0 diopters. Although such a wavefront sensor may not provide accurate measurements for diagnosing hyperopia (or determining a prescription for hyperopia), the wavefront sensor would provide more accurate measurements for diagnosing myopia (or determining a prescription for myopia) than a wavefront sensor that can cover both hyperopia and myopia (e.g., from −6.0 to +6.0 diopters). In addition, there are certain populations in which it is preferable to maintain a center of the range at a non-zero value. For example, in some Asian populations, the optical power may range from +6.0 to −14.0 diopters (with the center of the range at −4.0 diopters), whereas in some Caucasian populations, the optical power may range from +8.0 to −12.0 diopters (with the center of the range at −2.0 diopters). The center of the range can be shifted by moving the lenses (e.g., lens 124, lens 130, and/or the array of lenses 132). For example, defocusing light from eye 170 can shift the center of the range.

Device 100 further includes a corneal topographer. In some embodiments, the corneal topographer includes lens assembly 110, second light source 150, and second image sensor 160. In some embodiments, as shown in FIG. 1A, second image sensor 160 is distinct from first image sensor 140. In some embodiments, the wavefront sensor includes additional components.

Second light source 150 is configured to emit second light and transfer the second light emitted from second light source 150 toward eye 170. As shown in FIG. 1C, in some embodiments, second light source 150 is configured to transfer the second light emitted from second light source 150 toward eye 170 without transmitting the second light emitted from second light source 150 through lens assembly 110 (e.g., second light from second light source 150 is directly transferred to eye 170 without passing through lens assembly 110).

In some embodiments, device 100 includes beam steerer 126 configured to transfer light from eye 170, transmitted through lens assembly 110, toward first image sensor 140 and/or second image sensor 160. For example, when device 100 is configured for wavefront sensing (e.g., when light from first light source 120 is transferred toward eye 170), beam steerer 126 transmits light from eye 170 toward first image sensor 140, and when device 100 is configured for corneal topography (e.g., when light from second light source 150 is transferred toward eye 170), beam steerer 126 transmits light from eye 170 toward second image sensor 160.

Second light source 150 is distinct from first light source 120. In some embodiments, first light source 120 and second light source 150 emit light of different wavelengths (e.g., first light source 120 emits light of 900 nm wavelength, and second light source 150 emits light of 800 nm wavelength; alternatively, first light source 120 emits light of 850 nm wavelength, and second light source 150 emits light of 950 nm wavelength). In some embodiments, beam steerer 126 is a dichroic mirror (e.g., a mirror that is configured to transmit the first light from first light source 120 and reflect the second light from second light source 150, or alternatively, reflect the first light from first light source 120 and transmit the second light from second light source 150). In some embodiments, beam steerer 126 is a movable mirror (e.g., a mirror that can flip or rotate to steer light toward first image sensor 140 and second image sensor 160). In some embodiments, beam steerer 126 is a beam splitter. In some embodiments, beam steerer 126 is configured to transmit light of a first polarization and reflect light of a second polarization that is distinct from (e.g., perpendicular to) the first polarization. In some embodiments, beam steerer 126 is configured to reflect light of the first polarization and transmit light of the second polarization.

In some embodiments, second light source 150 is configured to project an array of spots on the eye. In some embodiments, the array of spots is arranged in a grid pattern (e.g., FIG. 7). In some embodiments, second light source 150 is configured to project light in a pattern of a plurality of concentric rings (e.g., Placido's disk).

In some embodiments, second light source 150 includes one or more light emitters 152 (e.g., light-emitting diodes) and diffuser 154 (e.g., a diffuser plate having an array of spots). Exemplary embodiments of second light source 150, which are configured to project an array of spots in accordance with some embodiments, are described below with respect to FIGS. 1D-1G.

Figure 1D:
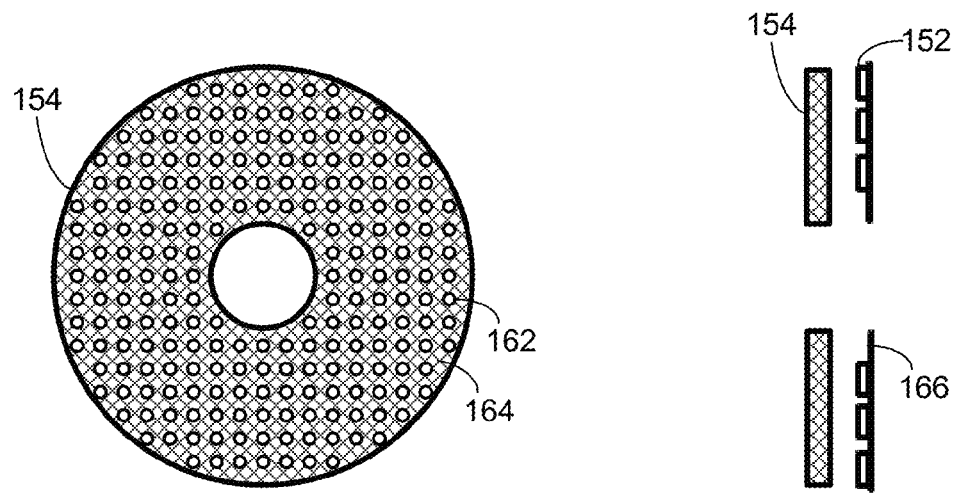
FIGS. 1D-1G illustrate light sources configured to project an array of spots in accordance with some embodiments.

FIG. 1D illustrates a front view (shown on the left-hand side of FIG. 1D) and a side view (shown on the right-hand side of FIG. 1D) of second light source 150 in accordance with some embodiments. In FIG. 1D, light emitters 152 mounted on mounting plate 166 are placed to face diffuser 154 so that light emitted from light emitters 152 are directed to a face of diffuser 154. Diffuser 154 includes a pattern 162 (e.g., an array of a grid as shown in FIG. 1D), through which light is transmitted (with diffusion). Diffuser 154 also includes portion 164 that blocks transmission of light. Thus, light from light emitters 152 passes through the pattern 162 and has the shape of the pattern 162.

Figure 1E:
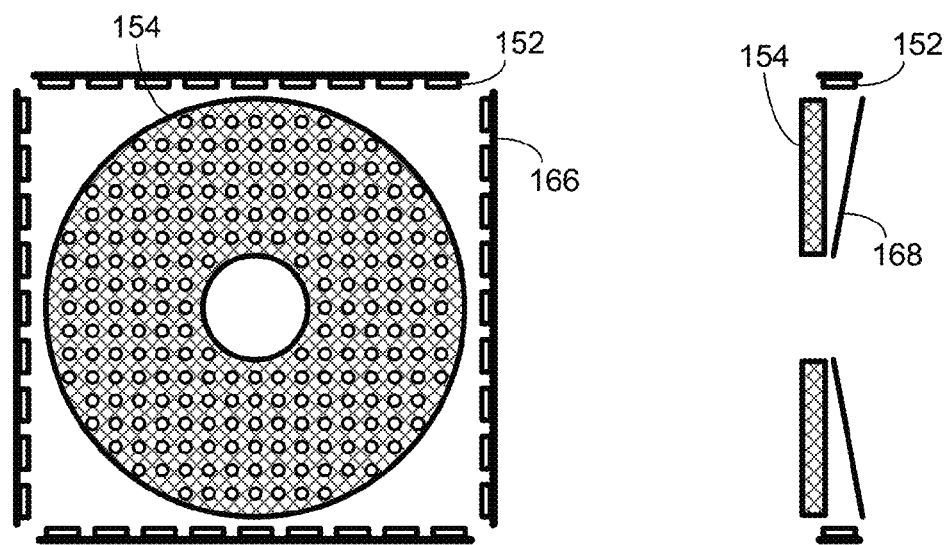
Figure 1F:
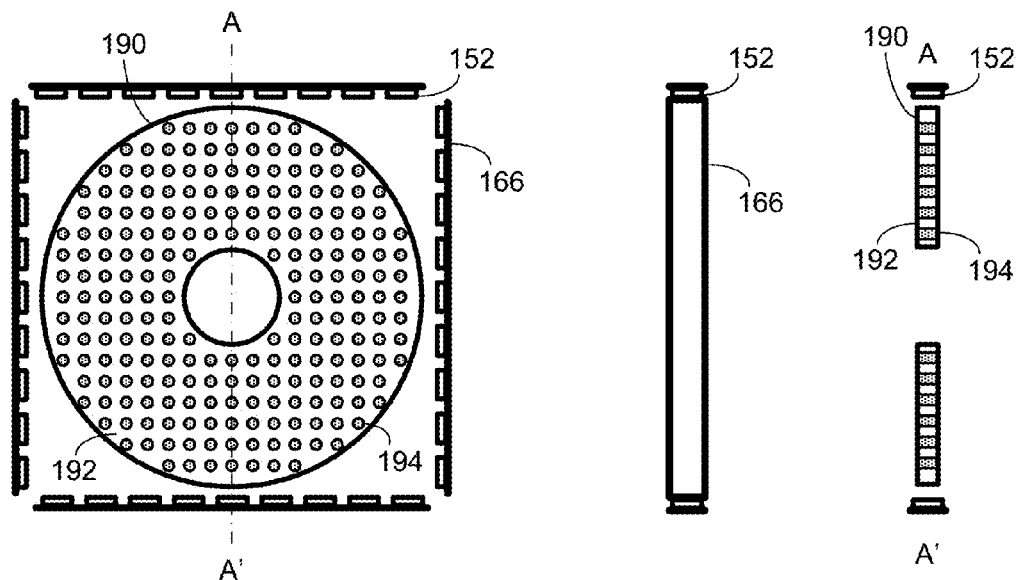
Figure 1G:
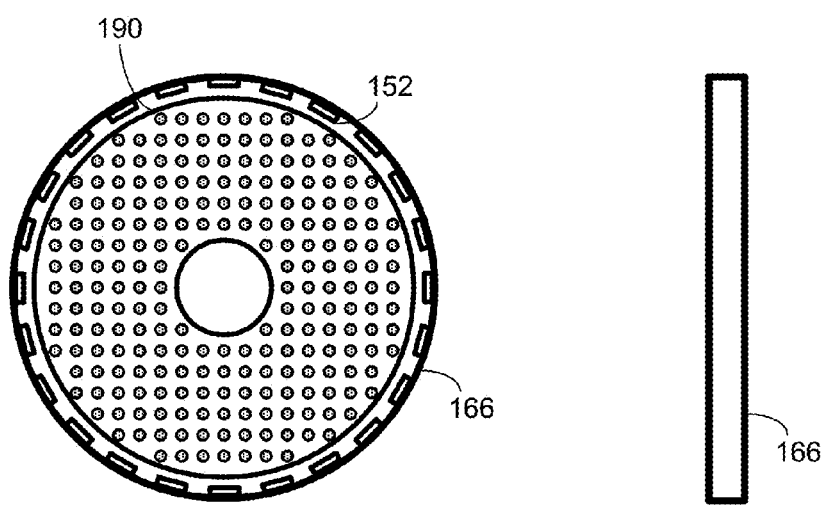

Compared to second light source 150 shown in FIG. 1D, second light sources 150 shown in FIGS. 1E-1G can have less thickness, which allows placement of lens assembly 110 closer to eye 170. The thickness of second light source 150 (and more importantly, the ability to place lens assembly 110 closer to eye 170) is important. The size of a center hole in diffuser 154 needs to be sufficiently small to project light from second light source 150 on a central part of cornea 172. However, if the size of the center hole in diffuser 154 is too small, only a small angle of light will be captured by lens assembly 110, which will reduce the reliability of wavefront sensing. Thus, one solution is to place lens assembly 110 as close toward eye 170, which allows lens assembly 110 to capture more light without actually changing the diameter of the center hole. In addition, placing lens assembly 110 closer toward eye 170 (e.g., as a first optical element to receive light from eye 170) allows capturing more light from eye 170, compared to placing a lens assembly after other optical elements (e.g., after beam steerer 122 or beam steerer 126).

FIG. 1E illustrates a front view (shown on the left-hand side of FIG. 1E) and a side view (shown on the right-hand side of FIG. 1E) of second light source 150 in accordance with some embodiments. In FIG. 1E, light emitters 152 are placed around diffuser 154 so that light from light emitters 152 is not sent directly to the face of diffuser 154. Instead, second light source 150 shown in FIG. 1E includes one or more mirrors (e.g., a conical mirror), which reflect light from second light source 150 toward the face of diffuser 154. Light from second light source 150 after passing through diffuser 154 has the shape of the pattern 162.

FIG. 1F illustrates a front view (shown on the left-hand side of FIG. 1F), a side view (shown in the middle of FIG. 1F), and a cross-sectional view (shown on the right-hand side of FIG. 1F) of second light source 150 in accordance with some embodiments. In FIG. 1F, second light source 150 includes light emitters 152 and diffuser 190. Diffuser 190 includes portion 192 that is transparent (e.g., optically transparent) to light from light emitters 152 and portion 194 that is configured to diffuse light from light emitters 152. Light emitters 152 are placed along a periphery of diffuser 190 so that light emitted from light emitters 152 are transferred toward the periphery of diffuser 190.

FIG. 1G is similar to FIG. 1F, except that light emitters 152 are arranged on round mounting plate 166 instead of square mounting plate 166.

Although diffusers 154 and 190 are each illustrated as a single component, in some embodiments, a diffuser includes multiple components (or multiple layers). For example, in some embodiments, a diffuser includes a diffusion layer configured to diffuse, spread out, or scatter light, and a separate masking layer for transmitting light in a particular pattern. The diffusion layer can be made from ground glass and/or light scattering material, such as photopolymer and/or polytetrafluoroethylene.

Turning back to FIG. 1A, second image sensor 160 is configured to receive light, from eye 170, transmitted through lens assembly 110. In some embodiments, the light from eye 170 includes light reflected from cornea 172 of eye 170 (in response to the second light from second light source 150). For example, as shown in FIG. 1C, light from eye 170 (e.g., light reflected from cornea 172) passes multiple optical elements, such as lens assembly 110, beam steerer 122, lens 124, beam steerer 126, and lenses 156 and 158, and reaches second image sensor 160.

The lenses in the corneal topographer (e.g., lens assembly 110 and lenses 124, 156, and 158) are configured to image a pattern of light projected on cornea 172 onto second image sensor 160. For example, when an array of spots is projected on cornea 172, the image of the array of spots detected by second image sensor 160 is used to determine the topography of cornea 172 (e.g., a profile of a surface of cornea 172 or a curvature of cornea 172).

Figure 1H:
FIG. 1H illustrates a portable device in accordance with some embodiments.

FIG. 1H illustrates device 100 in accordance with some embodiments. In FIG. 1H, device 100 includes eyecup 196. In some embodiments, eyecup 196 is configured to position the eye relative to the device. For example, eyecup 196 is configured to be placed against an orbit of the eye so that the eye is positioned for optical measurements, such as wavefront sensing and/or corneal topography measurements. Alternatively, in some embodiments, eyecup 196 is configured to block ambient light (e.g., with or without mechanically positioning the eye relative to device 100.

Figure 2:
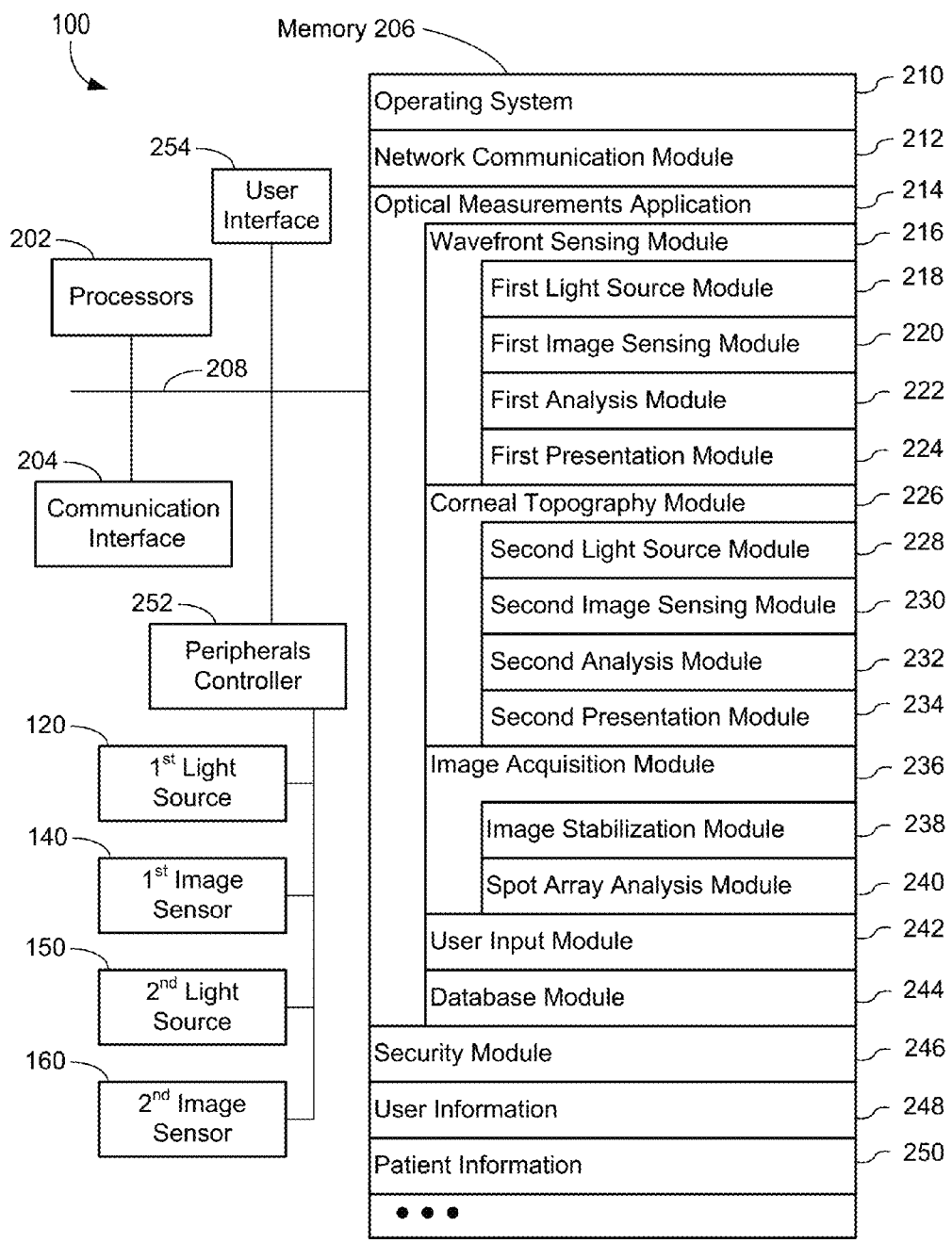
FIG. 2 is a block diagram illustrating electronic components of a portable device in accordance with some embodiments.

FIG. 2 is a block diagram illustrating electronic components of device 100 in accordance with some embodiments. Device 100 typically includes one or more processing units 202 (central processing units, application processing units, application-specific integrated circuit, etc., which are also called herein processors), one or more network or other communications interfaces 204, memory 206, and one or more communication buses 208 for interconnecting these components. In some embodiments, communication buses 208 include circuitry (sometimes called a chipset) that interconnects and controls communications between system components. In some embodiments, device 100 includes a user interface (e.g., a user interface having a display device, which can be used for displaying acquired images, one or more buttons, and/or other input devices). In some embodiments, device 100 also includes peripherals controller 252, which is configured to control operations of other electrical components of device 100, such as first light source 120, first image sensor 140, second light source 150, and second image sensor 160 (e.g., initiating respective light sources to emit light, and/or receiving information, such as images, from respective image sensors).

In some embodiments, communications interfaces 204 include wired communications interfaces and/or wireless communications interfaces (e.g., Wi-Fi, Bluetooth, etc.).

Memory 206 of device 100 includes high-speed random access memory, such as DRAM, SRAM, DDR RAM or other random access solid state memory devices; and may include non-volatile memory, such as one or more magnetic disk storage devices, optical disk storage devices, flash memory devices, or other non-volatile solid state storage devices. Memory 206 may optionally include one or more storage devices remotely located from the processors 202. Memory 206, or alternately the non-volatile memory device(s) within memory 206, comprises a computer readable storage medium (which includes a non-transitory computer readable storage medium and/or a transitory computer readable storage medium). In some embodiments, memory 206 includes a removable storage device (e.g., Secure Digital memory card, Universal Serial Bus memory device, etc.). In some embodiments, memory 206 or the computer readable storage medium of memory 206 stores the following programs, modules and data structures, or a subset thereof:

- operating system 210 that includes procedures for handling various basic system services and for performing hardware dependent tasks;
- network communication module (or instructions) 212 that is used for connecting device 100 to other computers (e.g., clients 302 and/or servers 304 shown in FIG. 3) via one or more communications interfaces 204 and one or more communications networks 306 (FIG. 3), such as the Internet, other wide area networks, local area networks, metropolitan area networks, and so on;
- optical measurements application 214 that controls operations of the light sources and the image sensors; and
- security module 246 that protects data stored on device 100 during its storage on device 100 and/or transmission to and from another computer (e.g., clients 302 and/or servers 304); for example, security module 246 may include an encryption module for encrypting data stored on device 100, a decryption module for decrypting encrypted data, either stored on device 100 or received from another computer, and an authentication module for authenticating a user of device 100 and/or a remote computer for communication with device 100 (e.g., for sending and/or receiving data).

In some embodiments, memory 206 also includes one or both of:

- user information 248 (e.g., information necessary for authenticating a user of device 100); and
- patient information 250 (e.g., optical measurement results and/or information that can identify patients whose optical measurement results are stored on device 100).

In some embodiments, optical measurements application 214 includes the following programs, modules and data structures, or a subset or superset thereof:

- wavefront sensing module 216 configured for operating the wavefront sensor in device 100;
- corneal topography module 226 configured for operating the corneal topographer in device 100;
- image acquisition module 236 configured for analyzing images collected by respective image sensors of device 100;
- user input module 242 configured for handling user inputs on device 100 (e.g., pressing of buttons of device 100, etc.); and
- database module 244 configured to assist storage of data on device 100 and retrieval of data from device 100 (in some embodiments, database module 244 operates in conjunction with security module 246).

In some embodiments, wavefront sensing module 216 includes the following programs and modules, or a subset or superset thereof:

- first light source module 218 configured for initiating first light source 120 (through peripherals controller 252) to emit light;
- first image sensing module 220 configured for receiving images from first image sensor 140;
- first analysis module 222 configured for analyzing images received from first image sensor 140; and
- first presentation module 224 configured for presenting measurement and analysis results from first analysis module 222 (e.g., graphically displaying images received from first image sensor 140, presenting aberrations shown in images received from first image sensor 140, sending the results to another computer, etc.).

In some embodiments, corneal topography module 226 includes the following programs and modules, or a subset or superset thereof:

- second light source module 228 configured for initiating second light source 150 (through peripherals controller 252) to emit light;
- second image sensing module 230 configured for receiving images from second image sensor 160;
- second analysis module 232 configured for analyzing images received from second image sensor 160; and
- second presentation module 234 configured for presenting measurement and analysis results from second analysis module 232 (e.g., graphically displaying images received from second image sensor 160, presenting cornea curvatures determined from images received from second image sensor 160, sending the results to another computer, etc.).

In some embodiments, image acquisition module 236 includes the following programs and modules, or a subset or superset thereof:

- image stabilization module 238 configured for reducing blurring during acquisition of images by image sensors; and
- spot array analysis module 240 configured for analyzing spot arrays (e.g., measuring displacements and/or disappearances of spots in the spot arrays).

In some embodiments, first image sensing module 220 initiates execution of image stabilization module 238 to reduce blurring during acquisition of images by first image sensor 140, and second image sensing module 230 initiates execution of image stabilization module 238 to reduce blurring during acquisition of images by second image sensor 160.

In some embodiments, first analysis module 222 initiates execution of spot array analysis module 240 to analyze spot arrays in images acquired by first image sensor 140, and second analysis module 232 initiates execution of spot array analysis module 240 to analyze spot arrays in images acquired by second image sensor 160.

Each of the above identified modules and applications correspond to a set of instructions for performing one or more functions described above. These modules (i.e., sets of instructions) need not be implemented as separate software programs, procedures or modules, and thus various subsets of these modules may be combined or otherwise re-arranged in various embodiments. In some embodiments, memory 206 may store a subset of the modules and data structures identified above. Furthermore, memory 206 may store additional modules and data structures not described above.

Figure 3:
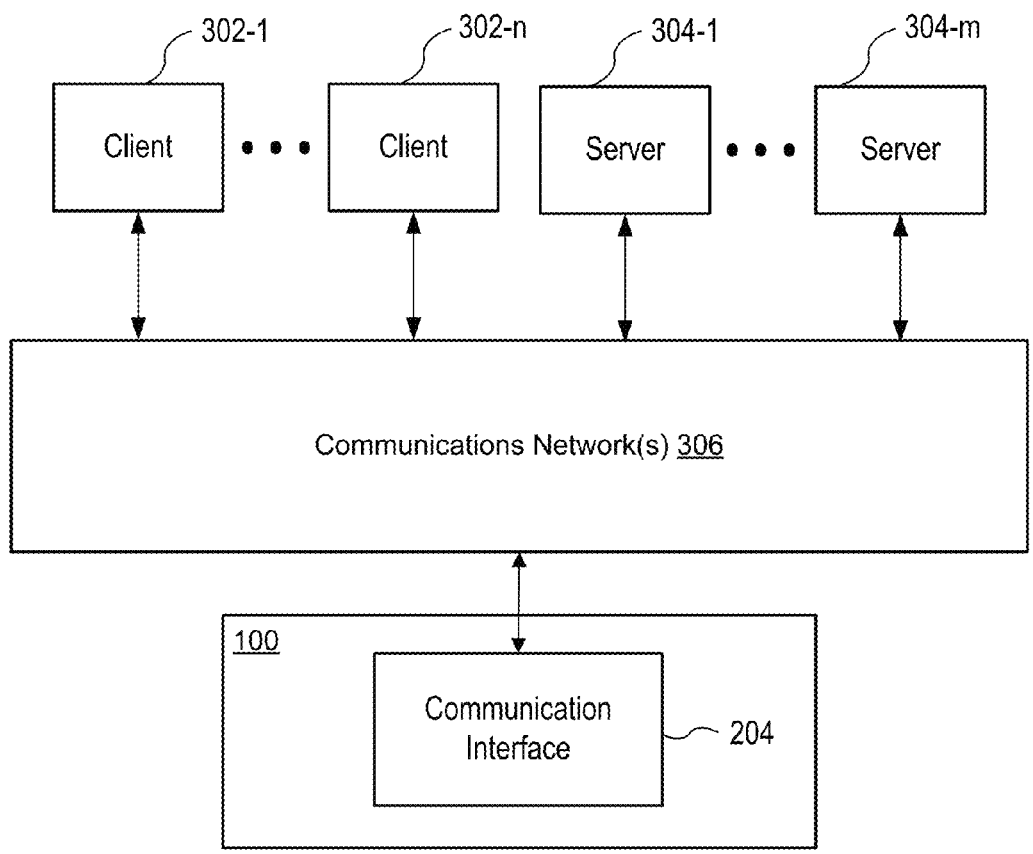
FIG. 3 is a block diagram illustrating a distributed computing system in accordance with some embodiments.

FIG. 3 is a block diagram illustrating a distributed computing system in accordance with some embodiments. In FIG. 3, the distributed computing system includes one or more client computers 302, one or more server systems 304, communications network 306, and device 100.

Client computers 302 can be any of a number of computing devices (e.g., Internet kiosk, personal digital assistant, cell phone, smart phone, gaming device, desktop computer, laptop computer, handheld computer, or combinations thereof) used to enable the activities described below. Client computer(s) 302 is also referred to herein as client(s). Client 302 typically includes a graphical user interface (GUI). In some embodiments, client 302 is connected to device 100 via communications network 106. As described in more detail below, the graphical user interface is used to display results from device 100 (e.g., acquired images and/or analysis results). In some embodiments, one or more clients are used to perform the analysis (for example, when device 100 does not include sufficient computational capabilities, images can be sent to one or more clients for analysis).

In some embodiments, the distributed computing system includes one or more server systems (also called server computers) 304 connected to communications network 306. One or more server systems 304 store results from device 100 (and a plurality of similar devices). For example, one or more server systems 304 store images transmitted from device 100 and/or analysis results. In some embodiments, one or more server systems 304 provide the stored images and/or analysis results to one or more clients (e.g., computers used by medical professionals) 302. In some embodiments, one or more server systems 304 are used to perform the analysis (e.g., the one or more servers analyze images sent by device 100).

In some embodiments, communications networks 306 are the Internet. In other embodiments, the communications networks 306 can be any local area network (LAN), wide area network (WAN), metropolitan area network, or a combination of such networks. In some embodiments, communications networks 306 include a wired network and/or a wireless network (e.g., Wi-Fi, Bluetooth, etc.).

In some embodiments, device 100 receives one or more software applications or one or more software modules from one or more server systems 304 or one or more clients 302 (e.g., using the wired communication network and/or the wireless communication network).

Notwithstanding the discrete blocks in FIGS. 2 and 3, these figures are intended to be a functional description of some embodiments, although, in some embodiments, the discrete blocks in FIGS. 2 and 3 can be a structural description of functional elements in the embodiments. One of ordinary skill in the art will recognize that an actual implementation might have the functional elements grouped or split among various components. In practice, and as recognized by those of ordinary skill in the art, items shown separately could be combined and some items could be separated. For example, in some embodiments, security module 246 is part of optical measurements application 214. In other embodiments, wavefront sensing module 216 and corneal topography module 226 are implemented as separate applications.

Figure 4:
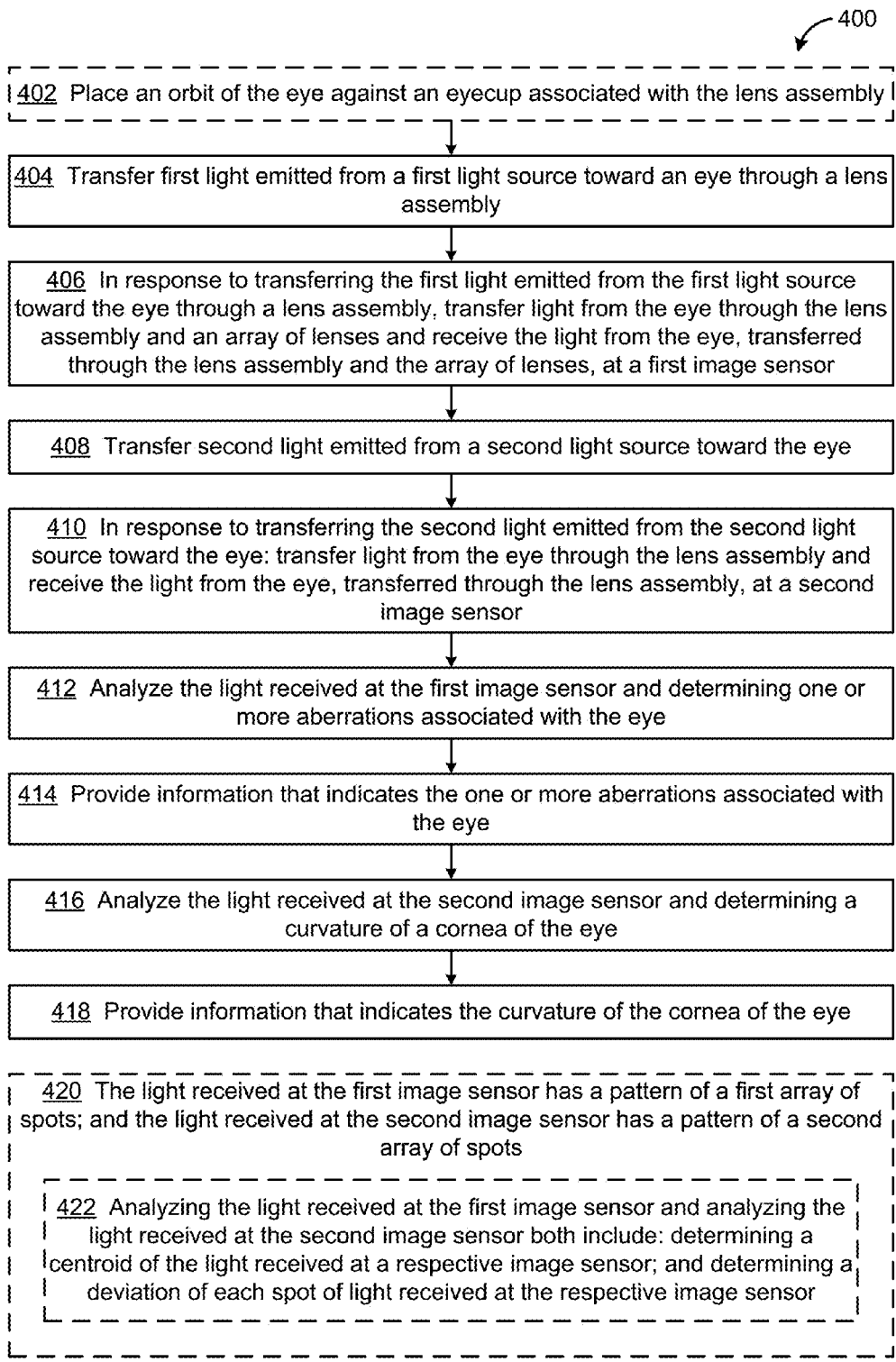
FIG. 4 is a flowchart representing a method of optical measurements with a portable device, in accordance with some embodiments.

FIG. 4 is a flowchart representing method 400 for optical measurements (e.g., wavefront sensing and keratometry (or corneal topography)) with a portable device, in accordance with some embodiments.

In some embodiments, method 400 includes (402) placing an orbit of the eye against an eyecup (e.g., eyecup 196 in FIG. 1H) associated with the lens assembly. In some embodiments, the eyecup blocks ambient light, which helps the pupil of the eye to dilate for more accurate wavefront sensing.

Method 400 includes (404) transferring first light emitted from a first light source toward the eye through a lens assembly, and, in response to transferring the first light emitted from the first light source toward the eye through a lens assembly, (406) transferring light from the eye through the lens assembly and an array of lenses; and receiving the light from the eye, transferred through the lens assembly and the array of lenses, at a first image sensor. For example, as shown in FIG. 1B, first light emitted from first light source 120 is transferred toward eye 170 through lens assembly 110. In response, light from eye 170 (e.g., light scattered and/or reflected from inside eye 170) is transferred through lens assembly 110 and the array of lenses 132, and is received at first image sensor 140.

In some embodiments, receiving the light from the eye at the first image sensor includes acquiring multiple images of the light from the eye with the first image sensor (e.g., multiple images are taken in a few seconds, or even in less than a second).

Method 400 also includes (408) transferring second light emitted from a second light source toward the eye, and, in response to transferring the second light emitted from the second light source toward the eye, (410) transferring light from the eye through the lens assembly; and receiving the light from the eye, transferred through the lens assembly, at a second image sensor. For example, as shown in FIG. 1C, second light emitted from second light source 150 is transferred toward eye 170. In response, light from eye 170 (e.g., light scattered and/or reflected from cornea 172 of eye 170) is transferred through lens assembly 110, and received at second image sensor 160. In some embodiments, receiving the light from the eye at the second image sensor includes acquiring multiple images of the light from the eye with the second image sensor.

Method 400 further includes (412) analyzing the light received at the first image sensor and determining one or more aberrations associated with the eye. For example, displacements and/or disappearances of spots in the image received at first image sensor 140 are measured and used to determine one or more aberrations associated with eye 170.

Method 400 includes (414) providing information that indicates the one or more aberrations associated with the eye. For example, a spherical aberration and an astigmatism of the eye (e.g., in diopter) can be reported.

Method 400 includes (416) analyzing the light received at the second image sensor and determining a curvature of a cornea of the eye; and (418) providing information that indicates the curvature of the cornea of the eye. In some embodiments, method 400 includes determining a corneal topography of the eye (e.g., determining a profile of the cornea of the eye). In some embodiments, method 400 includes determining the curvature of the cornea of the eye from the corneal topography of the eye. In some embodiments, method 400 includes determining two curvatures of the cornea (e.g., flat radius and steep radius) and providing information that indicates both curvatures of the cornea. In some embodiments, method 400 includes providing information that indicates a difference between the two curvatures and an angle of a respective radius with respect to a reference axis of the eye (e.g., a horizontal axis or a vertical axis). In some embodiments, method 400 includes providing information that indicates an average of the two curvatures.

In some embodiments, the light received at the first image sensor has (420) a pattern of a first array of spots; and the light received at the second image sensor has a pattern of a second array of spots. For example, the light received at first image sensor 140 has a pattern of an array of spots, because of the array of lenses 132 (e.g., each lens in the array of lenses 132 is responsible for a single spot on first image sensor 140). The light received at second image sensor 160 generally has a pattern of light projected on cornea 172 of eye 170 (e.g., FIG. 7). Unlike conventional corneal topographers, which utilize a pattern of concentric rings, a pattern of an array of spots can be projected on cornea 172 of eye 170, and the light received at second image sensor 160 also has a pattern of an array of spots. The use of an array of spots enables images acquired by second image sensor 160 to be analyzed in a similar manner as images acquired by first image sensor 140. In addition, it has been found that the use of a pattern of an array of spots for corneal topography further improves an accuracy of the corneal topography. Because an array of spots provides more discrete points to track, compared to conventional concentric rings, the resolution of corneal topography can be further improved with the use of a pattern of an array of spots.

In some embodiments, analyzing the light received at the first image sensor and analyzing the light received at the second image sensor both include (422): determining a centroid of the light received at a respective image sensor; and determining a deviation of each spot of light received at the respective image sensor. Thus, deviations (or displacements) of the spots are used to determine aberrations (in case of wavefront sensing) and/or deformations of the cornea (in case of corneal topography).

It should be understood that the particular order in which the operations in FIG. 4 have been described is merely exemplary and is not intended to indicate that the described order is the only order in which the operations could be performed. One of ordinary skill in the art would recognize various ways to reorder the operations described herein. For example, the analyzing operation (412) may be performed before the transferring operation (408). In another example, the analyzing operation (416) may be performed in conjunction with the analyzing operation (412), before the providing operation (414). Additionally, it should be noted that details of other processes described herein with respect to method 500 described herein are also applicable in an analogous manner to method 400 described above with respect to FIG. 4. For example, the transferring, receiving, and analyzing operations, described above with reference to method 400 optionally have one or more of the characteristics of the transferring, receiving, and analyzing operations described herein with reference to method 500 described herein. For brevity, these details are not repeated here.

FIG. 5 is a flowchart representing method 500 of optical measurements (e.g., wavefront sensing and keratometry (or corneal topography)) with a portable device, in accordance with some embodiments.

Method 500 is performed at an electronic device (e.g., device 100) that includes one or more processors (e.g., processors 202, FIG. 2) and memory (e.g., memory 206, FIG. 2) storing instructions for execution by the one or more processors.

Method 500 includes (502) initiating a first light source to emit first light (e.g., using first light source module 218 to initiate first light source 120 to emit first light). The first light emitted from the first light source is transferred toward an eye through a lens assembly. For example, as shown in FIG. 1B, the first light emitted from first light source 120 is transferred toward eye 170 through lens assembly 110.

Method 500 includes, while the first light source emits the first light, (504) receiving, at a first image sensor, a first image of light from the eye, transferred through the lens assembly and an array of lenses (e.g., using first image sensing module 220).

Method 500 includes (506) initiating a second light source to emit second light (e.g., using second light source module 228 to initiate second light source 150 to emit second light). The light emitted from the second light source is transferred toward the eye. For example, as shown in FIG. 1C, the second light emitted from second light source 10 is transferred toward eye 170.

Method 500 includes (508), while the second light source emits the second light, receiving, at a second image sensor, a second image of light from the eye, transferred through the lens assembly (e.g., using second image sensing module 230).

In some embodiments, method 500 includes, in conjunction with receiving the second image of the light from the eye, (510) collecting an image of the eye with the second image sensor. For example, an image of the eye is acquired with second image sensor 160. This image can be used to determine whether the eye is properly positioned for optical measurements (e.g., wavefront sensing and/or corneal topography). In some embodiments, the image of the eye is collected with the second image sensor in temporal proximity to receiving the second image of the light from the eye. This reduces any error due to the movement of the eye between collecting the image of the eye and receiving the second image. For example, the image of the eye is collected with the second image sensor immediately before receiving the second image of the light from the eye. Alternatively, the image of the eye is collected with the second image sensor immediately after receiving the second image of the light from the eye. In some embodiments, method 500 includes providing the image of the eye for display to a user and receiving a user input (e.g., pressing on a "go" or "acquire" button) to initiate receiving the second image.

In some embodiments, method 500 includes (512) confirming whether a location of the eye satisfies predefined alignment criteria. For example, method 500 includes determining that the eye is offset from the center of the image by more than a distance, and in response, providing a warning (e.g., either a visible or audible warning to indicate that the second image may not be usable or the result may not be accurate) and/or preventing receiving of the second image.

Figure 6:
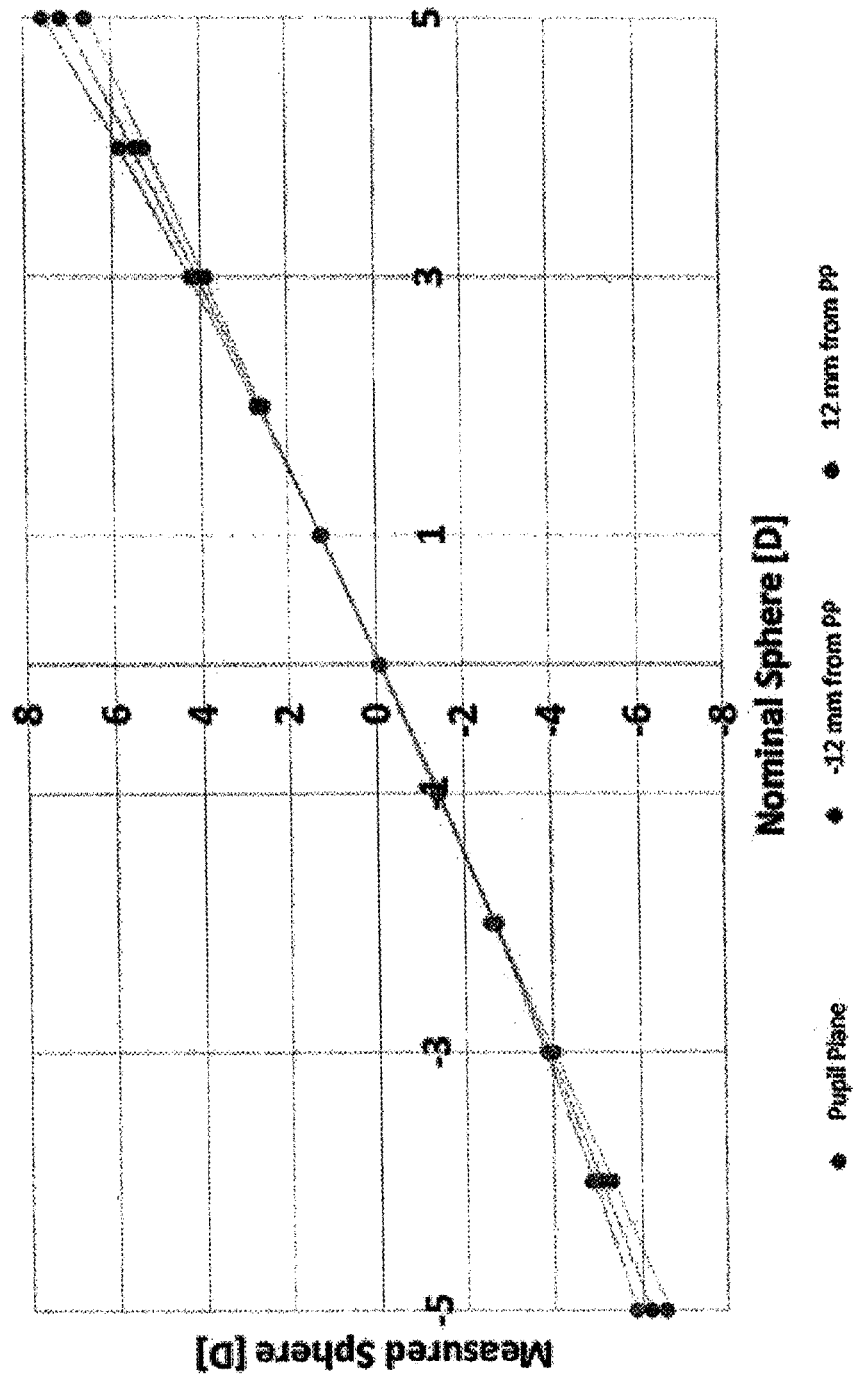
FIG. 6 illustrates exemplary calibration curves for adjusting one or more aberrations of an eye based on a position of the eye relative to the device, in accordance with some embodiments.

In some embodiments, method 500 includes (514) determining a position of the eye from the image of the eye collected with the second image sensor; and adjusting one or more aberrations associated with the eye based on the position of the eye determined from the image of the eye collected with the second image sensor. The inventors of this application have found that the measurement of the power of the eye is incorrect if the eye is placed away from a pupil plane of device 100. The inventors of this application have also discovered that the error can be corrected if the distance from the eye to the pupil plane of device 100 is known. FIG. 6 illustrates exemplary calibration curves that can be used to calibrate the measurements. For example, if the eye is positioned away from the pupil plane of device 100 by 12 mm, the measured power of the eye may be off by approximately 10%. Thus, the measured power of the eye should be adjusted accordingly.

In some embodiments, method 500 includes (516) determining a size of a pupil of the eye from the image of the eye collected with the second image sensor. This allows a user of device 100 to ensure that the pupil size is sufficient to measure high order aberrations, because high order aberrations are difficult to measure if the pupil size is not sufficiently large.

In some embodiments, method 500 includes: (518) analyzing the first image and determining one or more aberrations associated with the eye (e.g., determining spherical aberrations and astigmatism of the eye); and analyzing the second image and determining a curvature of a cornea of the eye. In some embodiments, determining the curvature of the cornea of the eye includes determining a corneal topography of the eye.

In some embodiments, the instructions include a predefined set of instructions for analyzing an image that includes an array of spots (e.g., spot array analysis module 240 in FIG. 2). Analyzing the first image and determining the one or more aberrations associated with the eye include (520) executing the predefined set of instructions for analyzing an image that includes an array of spots; and analyzing the second image and determining the curvature of the cornea of the eye also include executing the predefined set of instructions for analyzing an image that includes an array of spots. Because the same predefined set of instructions is used for analyzing both images received at the first image sensor and at the second image sensor, the software application can be made smaller, faster, and more efficient.

It should be understood that the particular order in which the operations in FIG. 5 have been described is merely exemplary and is not intended to indicate that the described order is the only order in which the operations could be performed. One of ordinary skill in the art would recognize various ways to reorder the operations described herein. Additionally, it should be noted that details of other processes described herein with respect to method 400 described herein are also applicable in an analogous manner to method 500 described above with respect to FIG. 5. For example, the transferring, receiving, and analyzing operations, described above with reference to method 500 optionally have one or more of the characteristics of the transferring, receiving, and analyzing operations described herein with reference to method 400 described herein. For brevity, these details are not repeated here.

FIG. 6 illustrates exemplary calibration curves for adjusting one or more aberrations of an eye based on a position of the eye relative to the device, in accordance with some embodiments. In FIG. 6, each curve represents measured spherical powers of simulated eyes (e.g., simulated by representative lenses of known powers) as functions of their true (nominal) spherical powers. The curves shown in FIG. 6 also indicate that the measured spherical powers of the simulated eyes vary depending on the position of the eye. As explained above, if the eye is positioned away from the pupil plane of device 100 by 12 mm, the measured power of the eye can be off by as much as 10%. By using the calibration curves shown in FIG. 6, the true spherical power of an eye can be determined. Furthermore, the error caused by the position of the eye can be reduced.

Figure 7:
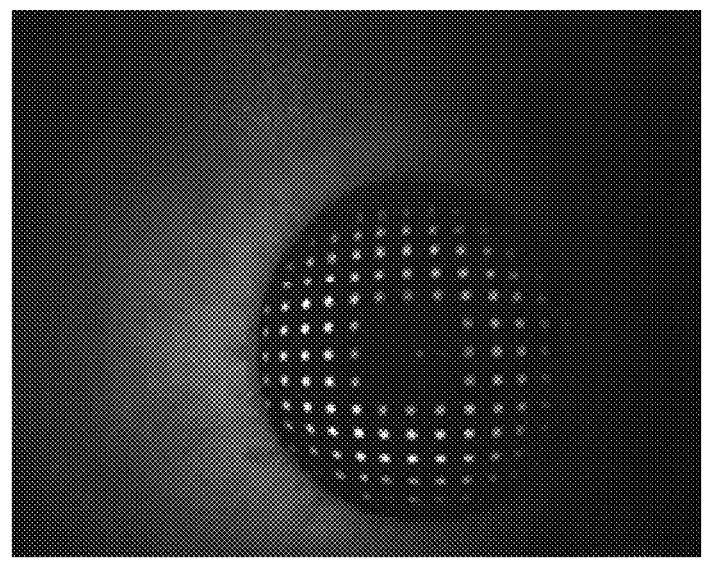
FIG. 7 is an exemplary image of an eye with projection of a spot array pattern in accordance with some embodiments.

FIG. 7 is an exemplary image of an eye with projection of a spot array pattern in accordance with some embodiments. As shown in FIG. 7, the sport array pattern has a shape of a grid, unlike concentric circles used in conventional Placido corneal topographers. As described above, the use of the spot array pattern improves the accuracy of corneal topography, and also improves the processing of images for corneal topography by portable devices, because the same set of instructions can be used for analyzing both images for wavefront sensing and images for corneal topography. The details of using the spot array pattern, which are described above, are not repeated here.

The foregoing description, for purpose of explanation, has been described with reference to specific embodiments. However, the illustrative discussions above are not intended to be exhaustive or to limit the scope of claims to the precise forms disclosed. Many modifications and variations are possible in view of the above teachings. The embodiments were chosen and described in order to best explain the principles of the various described embodiments and their practical applications, to thereby enable others skilled in the art to best utilize the invention and the various described embodiments with various modifications as are suited to the particular use contemplated.

What is claimed is:

1. A method performed by a portable device comprising a lens assembly, a wavefront sensor, and a keratometer, the method comprising:

transferring first light emitted from a first light source toward an eye through the lens assembly;

in response to transferring the first light emitted from the first light source toward the eye through a lens assembly:

transferring light from the eye through the lens assembly and an array of lenses; and receiving the light from the eye, transferred through the lens assembly and the array of lenses, at a first image sensor;

transferring second light emitted from a second light source toward the eye;

in response to transferring the second light emitted from the second light source toward the eye:

transferring light from the eye through the lens assembly; and receiving the light from the eye, transferred through the lens assembly, at a second image sensor;

analyzing the light received at the first image sensor and determining one or more aberrations associated with the eye;

providing information that indicates the one or more aberrations associated with the eye;

analyzing the light received at the second image sensor and determining a curvature of a cornea of the eye; and providing information that indicates the curvature of the cornea of the eye, wherein:

the light received at the first image sensor has a pattern of a first array of spots;

the light received at the second image sensor has a pattern of a second array of spots;

analyzing the light received at the first image sensor and analyzing the light received at the second image sensor both include:

determining a centroid of the light received at a respective image sensor; and determining a deviation of each spot of light received at the respective image sensor.

2. The method of claim 1, including:
placing an orbit of the eye against an eyecup associated with the lens assembly.

3. The method of claim 1, wherein:
the wavefront sensor includes:
  the lens assembly;
  the first light source configured to emit first light and transfer the first light emitted from the first light source toward the eye through the lens assembly;
  the array of lenses that is distinct from the lens assembly; and
  the first image sensor configured to receive light, from the eye, transmitted through the lens assembly and the array of lenses; and
the keratometer includes:
  the lens assembly;
  the second light source that is distinct from the first light source and configured to emit second light and transfer the second light emitted from the second light source toward the eye; and
  the second image sensor configured to receive light, from the eye, transmitted through the lens assembly.

4. The method of claim 3, wherein the second light source is configured to transfer the second light emitted from the second light source toward the eye without transmitting the second light emitted from the second light source through the lens assembly.

5. The method of claim 3, wherein the second light source is configured to project an array of spots on the eye.

6. The method of claim 3, wherein the second light source includes a diffuser with a spot array pattern and one or more light emitters placed behind the diffuser and configured to emit light toward the diffuser.

7. The method of claim 3, wherein the second light source includes a diffuser with a spot array pattern and one or more light emitters and one or more reflectors arranged to send light toward the diffuser from behind the diffuser.

8. The method of claim 3, wherein the second light source includes a diffuser with a spot array pattern and a plurality of light emitters placed along a periphery of the diffuser, wherein at least a first portion of the diffuser is transparent and at least a second portion of the diffuser is configured to diffuse light.

9. The method of claim 3, wherein the lens assembly includes a lens that is tilted from an optical axis of the device.

10. The method of claim 3, wherein the first light source is configured to transfer the first light emitted from the first light source off an optical axis of the device.

11. The method of claim 3, wherein the first image sensor is configured to receive the light from the eye while the first light source emits the first light.

12. The method of claim 3, wherein the second image sensor is configured to receive the light from the eye while the second light source emits the second light.

13. The method of claim 3, wherein the lens assembly is a doublet lens.

14. The method of claim 3, wherein the lens assembly includes two or more separate lenses.

15. The method of claim 3, wherein the device includes:
a beam steerer configured to transfer light from the eye, transmitted through the lens assembly, toward the first image sensor and/or the second image sensor.

16. The method of claim 15, wherein the beam steerer is a beam splitter.

17. The method of claim 3, wherein the device includes:
an eyecup configured to position the eye relative to the device.

18. A portable device, comprising:
a wavefront sensor that includes:
  a first light source configured to emit first light and transfer the first light emitted from the first light source toward an eye through the lens assembly;
  an array of lenses; and
  a first image sensor configured to receive light, from the eye, transmitted through the lens assembly and the array of lenses, wherein the light received at the first image sensor has a pattern of a first array of spots; and
a keratometer that includes:
  a second light source that is distinct from the first light source and configured to emit second light and transfer the second light emitted from the second light source toward the eye, wherein the second light source is configured to project an array of spots on the eye; and
  a second image sensor configured to receive light, from the eye, transmitted through the lens assembly, wherein the light received at the second image sensor has a pattern of a second array of spots,
wherein the portable device is configured to:
  analyze the light received at the first image sensor and analyze the light received at the second image sensor, both including:
    determining a centroid of the light received at a respective image sensor; and
    determining a deviation of each spot of light received at the respective image sensor.

\* \* \* \* \*